US006627610B1

(12) United States Patent
Glenn

(10) Patent No.: US 6,627,610 B1
(45) Date of Patent: Sep. 30, 2003

(54) METHOD FOR INHIBITION OF VIRAL MORPHOGENESIS

(76) Inventor: Jeffrey Glenn, 1130 Welch Rd., Palo Alto, CA (US) 94304

( * ) Notice: Subject to any disclaimer, the term of this patent is extended or adjusted under 35 U.S.C. 154(b) by 48 days.

(21) Appl. No.: 09/687,267

(22) Filed: Oct. 13, 2000

Related U.S. Application Data

(60) Division of application No. 09/028,655, filed on Feb. 24, 1999, now Pat. No. 6,159,939, which is a continuation of application No. 08/347,448, filed as application No. PCT/US93/05247 on Jun. 1, 1993, now Pat. No. 5,876,920, which is a continuation-in-part of application No. 07/890,754, filed on May 29, 1992, now Pat. No. 5,503,973.

(51) Int. Cl.[7] ............................................. A61K 38/00
(52) U.S. Cl. ............................ 514/18; 514/12; 514/13; 514/14; 514/15; 514/16; 514/17
(58) Field of Search ........................... 514/12, 13, 14, 514/15, 16, 17, 18

(56) References Cited

U.S. PATENT DOCUMENTS

| H1345 H | 8/1994 | Biller | ........................ 514/108 |
| 5,503,973 A | 4/1996 | Glenn | ........................... 435/5 |

FOREIGN PATENT DOCUMENTS

WO    WO 94/23041    10/1994

OTHER PUBLICATIONS

Benet et al., "Pharmacokinetics: The Dynamics of Drug Absorption, Distribution, and Elimination", pp. 3–32 in The Pharmacological Basis of Therapeutics, Eighth Ed., McGraw–Hill, Inc., New York, 1990.*
Rice et al., "Discovery and in Vitro Development of AIDS Antiviral Drugs as Biopharmaceuticals", Advances in Pharmacology 33:389–438, 1995.*
American Heritage College Dictionary (3rd. Ed.) Houghton Mifflin Company, Boston and New York, p. 866.
Beck et al., "Incorporation of a Product of Mevalonic Acid Metabolism into Proteins of Chinese Hamster Ovary Cell Nuclei," *Journal of Cell Biology* (1988) 107:1307–1316.
Bruss et al., "Mutation Analysis of Hepatitis B Surface Antigen Particle Assembly and Secretion," *J. Virol* (1991) 65(7):3813–3820.
Bukhtiyarov et al., "Photoreactive Analogues of Prenyl Diphosphates as Inhibitors and Probes of Human Protein Farnesyltransferase and Geranyltransferase Type I," *J Biol Chem* (1995) 270(32):19035–19040.
Derwent Pub. Ltd., London.: Database WPI; Sec. Ch, Week 9430 (Feb. 1, 1996).
Detroy et al., "Patulin Inhibition of Mycovirus Replication in *Penicilluim stoloniferum,*" *J Gen Micro* (1975) 92:167–174.

Finegold et al., "Common Modifications of Trimeric G Proteins and Ras Protein: Involvement of Polyisoprenylation," *Science* (1990) 249:165–169.
Gibbs, "Ras C–Terminal Processing Enzymes–New Drug Targets?" *Cell* (1991) 65:1–4.
Glenn et al., "trans–Dominant Inhibition of Human Hepatitis Delta Virus Genome Replication," *J Virol* (1991) 65(5): 2357–2361.
Glenn et al., "Use of Prenylation Inhibitor as a Novel Antiviral Agent," *J Virol* (1998) 72(11):9303–9306.
Glenn et al., "Identification of a Prenylation Site in Delta Virus Large Antigen," *Science* (1992) 256:1331–1333.
Glomset et al., "Prenyl Proteins in Eukaryotic Cells: a New Type of Membrane Anchor," *TIBS* Reviews (1990) 15:139–142.
Hancock et al., "All ras Proteins are Polyisoprenylated but Only Some are Palmitoylated," *Cell* (1989) 57:1167–1177.
Hoffman, "Playing Tag With Membrane Proteins," *Science* (1991) 254:650–651.
Hruby et al., "Lipid Modification of Vaccinia Virus Proteins," Abstracts of the American Society for Microbiology, 92nd General Meeting, p. 400 (May 1992).
Kaminchik et al., "Genetic Characterization of Human Immunodeficiency Virus Type 1 Nef Gene Products Translated In Vitro and Expressed in Mammalian Cells," *J Virology* (1995) 65(2):583–588.
Kestler et al., "Importance of the nef Gene for Maintenance of High Virus Loads and for Development of AIDS," *Cell* (1991) 65:651–662.
Kitamura et al., "Primary Structure, Gene Organization and Polypeptide Expression of Poliovirus RNA," *Nature* (1981) 291: 547–553.
Kohl et al., "Selective Inhibition of Ras–Dependent Transformation by a Farnesyltransferase Inhibitor," *Science* (1993) 260:1934–1937.
Koff, "Prenylation of the Large Hepatitis Delta Virus Antigen: A Target for Antiviral Therapy," *Gastroenterology* (1992) 103:1978–1986.
Maltese, "Posttranslational Modification of Proteins by Isoprenoids in Mammalian Cells," *FASEB Journal* (1990) 4:3319–3328.
Miura et al., "Inhibition of Protein Prenylation by Patulin," *FEBS Letters* (1993) 318:88–90.
Moores et al., "Sequence Dependence of Protein Isoprenylation," *J Biol Chem* (1991) 266(22):14603–14610.

(List continued on next page.)

*Primary Examiner*—Brenda Brumback
(74) *Attorney, Agent, or Firm*—Morrison & Foerster LLP

(57) ABSTRACT

Viral morphogenesis, production, release or uncoating can be inhibited by effecting inhibition of prenylation of, or inhibition of post-prenylation reactions of, at least one viral protein. The use of inhibitors of prenylation, and post-prenylation reactions, for example, inhibitors of the mevalonate and prenyl group synthesis pathways, inhibitors of prenyl group transferases and mimics of the prenylation target CXXX box are disclosed.

9 Claims, 2 Drawing Sheets

OTHER PUBLICATIONS

Overmeyer et al., "Isopernoid Requirement for Intracellular Transport and Processing of Murine Leukemia Virus Envelope Protein," *J Biol Chem* (1992) 267(31):22686–22692.

Oxford Dictionary of Biochemistry and Molecular Biology (Oxford University Press, Oxford (1997)) p. 440.

Pompliano et al., "Steady–State Kinetic Mechanism of Ras Farnesyl: Protein Transferase," *Biochemistry* (1992) 31:3800–3807.

Poradosu et al., "Alpha–Cyanocinnamide Derivatives: a New Family of Non–Peptide, Non–Sulfhydryl Inhibitors of Ras Farnesylation," *Bioorg Med Chem* (1999) 7(8):1727–1736.

Ratner et al., "Nef," *Current Topics Microbiol Immunol* (1995) 193:169–203.

Reiss et al., "Inhibition of Purified p21 Ras Farnesyl: Protein Transferase by Cys–AAX Peptides," *Cell* (1990) 62:81–88.

Rightsel et al., "Antiviral Activity of Gliotoxin and Gliotoxin Acetate," *Nature* (1964) 204:1333–1334.

Schafer et al., "Genetic and Pharmacological Suppression of Oncogenic Mutations in Ras Genes of Yeast and Humans," *Science* (1989) 245:379–385.

Scholten et al., "Synergy Between Anions and Farnesyl-diphosphate Competitive Inhibitors of Farnesyl: Protein Transferase," *J Biol Chem* (1997) 272(29):18077–18081.

Silverman et al., "Oreganic Acid, a Potent Inhibitor of Ras Farnesyl–Protein Transferase," *Biochem Biophys Res Commun* (1997) 232(2):478–481.

Stedman's Medical Dictionary (24th Ed.) Williams & Wilkins, Baltimore, p. 889 (1982).

Stedman's Medical Dictionary (27th Ed.) Lippincott Williams & Wilkins, Baltimore, p. 1112 (2000).

Stirtan and Poulter, "Yeast Protein Geranylgeranyltransferase Type I: Steady–State Kinetics and Substrate Binding," *Biochemistry* (1997) 36(15):4552–4557.

Trono, "HIV Accessory Proteins: Leading Roles for the Supporting Cast," *Cell* (1995) 82:189–192.

Van der Pyl et al., "Inhibition of Farnesyl–Protein Transferase by Gliotoxin and Acetylgliotoxin," *J Antibiotics* (1992) 45:1802–1805.

Wang et al., "Small–Form Hepatitis B Surface Antigen is Sufficient to Help in the Aseembly of Hepatitis Delta Virus–Like Particles," *J Virol* (1991) 65:6630–6636.

Bergman, K. (1986). *J Infect Dis* 154:702–706.

Bonino, F. et al. (1984). *Infection & Immunity* 43:1000–10005.

Bonino, F. et al. (1986). *J Virol* 58:945–950.

Chao, M. et al. (1990). *J Virol* 64:5066–5069.

Chao, Y.–C., et al. (1991). *Hepatology* 13:345–352.

Deny, P. et al. (1991). *J Gen Virol* 72:735–739.

Ellens, H. et al. (1989). *Methods Cell Biol* 31:155–176.

Glenn, J. et al. (1990). *J Virol* 64:3104–3107.

Glenn, J. et al. (1991). *J Virol* 65:2357–2361.

Glenn, J. (1992). Thesis, University of California, San Francisco, pp. 105,107.

Glenn, J. (1993). *Progress in Clinical and Biological Research* 382:53–60.

Glenn, J. In The Unique Hepatitis Delta Virus (G. Dinter–Gottlieb ed.), 1995, pp. 81–93. R.C. Landes Company, Austin, Texas.

Hoffnagle, J. (1989). *J Am Med Assoc.* 261:1321–1325.

Imazeki, F. et al. (1990). *J Virol* 64:5594–5599.

Keller, R. (1986). *J Biol Chem* 261:12053–12059.

Krieg, P. and Melton D. (1984). *Nucleic Acid Res* 12:7057–7070.

Kuo, M. et al. (1988). *J Virol* 62:1855–1861.

Kuo, M. et al. (1989). *J Virol* 63:1945–1950.

Lin, J.–H. et al. (1990). *J Virol* 64:4051–4058.

Luo, G. et al. (1990). *J Virol* 64:1021–1027.

Makino, S. et al. (1987). *Nature* 329:343–346.

Ramig, R. (1990). *Virology* 95–112.

Rizetto, M. (1980). *J Infect Dis* 141:590–602.

Rizetto, M. (1980). *Proc Natl Acad Sci USA* 77:6124–6128.

Rizetto, M. (1983). *Hepatology* 3:729–737.

Ryu, W.–S., et al. (1992). *J Virol* 66:2310–2315.

Saldanha, J. et al. (1990). *J Gen Virol* 71:1603–1606.

Wang, K.–S., et al. (1986). *Nature* 323:508–514.

Xia, Y. et al. (1990). *Virology* 178:331–336.

\* cited by examiner

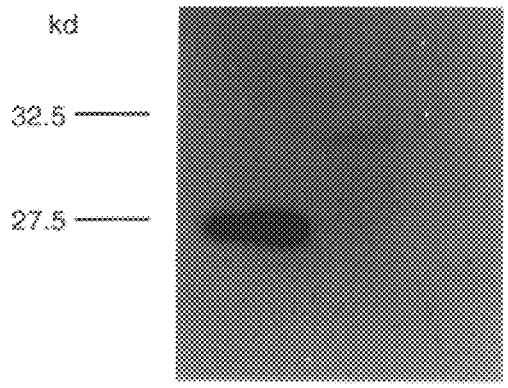
FIG._1A
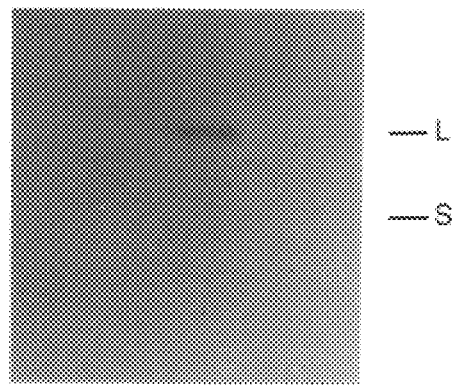
FIG._1B
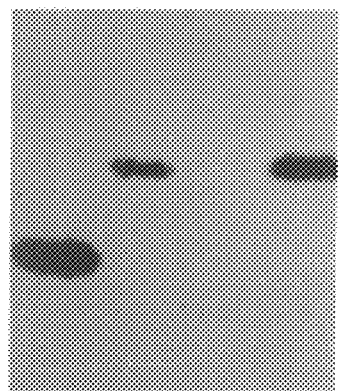
FIG._2A
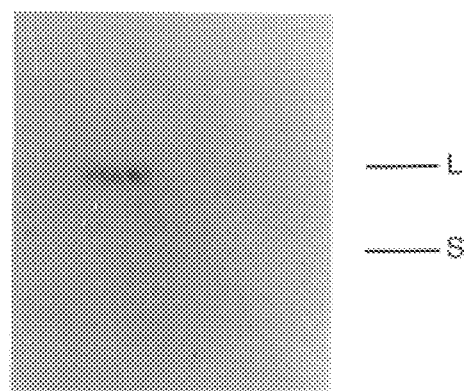
FIG._2B

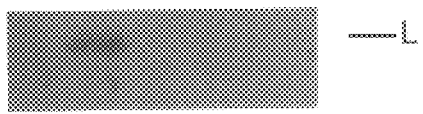
1  2  3
FIG._3A
4  5  6
FIG._3C
32.6 —
37.5 —
1  2  3
FIG._3B
4  5  6
FIG._3D
SMALL ANTIGEN
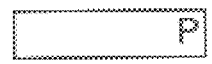
ENHANCES GENOME REPLICATION
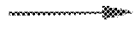
LARGE ANTIGEN
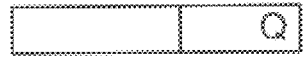
INHIBITS GENOME REPLICATION
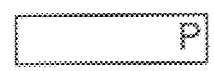
NO PARTICLE FORMATION WITH HBsAG
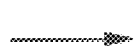
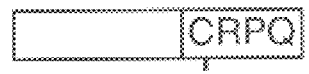
PRENYLATED PARTICLE FORMATION WITH HBsAG
GENOME REPLICATION  PACKAGING
FIG._4

METHOD FOR INHIBITION OF VIRAL MORPHOGENESIS

This application is a divisional of U.S. Ser. No. 09/028,655, filed Feb. 24, 1999, now U.S. Pat. No. 6,159,939, which is a continuation of U.S. Ser. No. 08/347,448, filed Jun. 23, 1995, now U.S. Pat. No. 5,876,920, which is a 371 of PCT/US93/05247, filed Jun. 1, 1993, which is a Continuation-in-Part of U.S. Ser. No. 07/890,754, filed May 29, 1992, now U.S. Pat. No. 5,503,973.

This invention was made with the support of the National Institutes of Health. The United States Government has a certain rights in this invention.

TECHNICAL FIELD

The invention is directed to inhibiting viral morphogenesis and viral infection. In particular, it concerns effecting such inhibition by inhibiting the prenylation or post prenylation reactions of a viral protein.

BACKGROUND ART

It has been shown that certain membrane-associated proteins require the addition of lipophilic residues in order to function properly. One family of such modifications is termed "prenylation" because the hydrophobic residue is derived from isoprenoid precursors. The prenyl residue is known to attach to the sulfhydryl group of a cysteine which has been shown in a number of membrane-associated proteins to be contained in a "CXXX" (SEQ ID NO: 1) box at the carboxy terminus of the substrate protein. In particular, one such membrane-associated protein has been shown to be the protein product of the ras oncogene. Summaries of these reactions conferring hydrophobic properties on membrane proteins, including prenylation, have appeared by Hoffman, M., *Science* (1991) 254:650–651, and by Gibbs, J. B., *Cell* (1991) 65:1–4.

In addition, in many cases, prenylation is a first step in a series of further reactions which modify the carboxy terminus of prenylated proteins. These prenylation initiated, or post-prenylation reactions include carboxymethylation and proteolysis.

In the prenylation substrate proteins studied to date, the CXXX (SEQ ID NO: 1) box contains aliphatic residues in the second and third positions and a leucine, serine, methionine, cysteine or alanine in the terminal position. Thus, in the CXXX (SEQ ID NO: 1) boxes so far studied, the box itself is relatively hydrophobic.

It has now been found that prenylation of a viral protein is necessary for the morphogenesis of hepatitis delta virus (HDV). This is the first demonstration that viral proteins are subject to prenylation. Furthermore, certain functional consequences can be ascribed to prenylation. The viral protein which is the target of prenylation, surprisingly, contains a hydrophilic CXXX (SEQ ID NO: 1) box of the sequence Cys-Arg-Pro-Gln (SEQ ID NO: 2). Prenylation, or prenylation-initiated modification, of this relatively hydrophilic CXXX (SEQ ID NO: 1) box and corresponding CXXX (SEQ ID NO: 1) boxes (hydrophilic or otherwise) or other cysteine-containing sequences near the C-terminus of proteins in other virions are suitable targets for antiviral strategies.

These targets can now be seen to include, but are not limited to, proteins of hepatitis A virus (HAV), hepatitis C virus (HCV), herpes simplex virus (HSV), cytomegalovirus (CMV), varicella-zoster virus (VZV), influenza virus, plant viruses such as tobacco mosaic satellite virus (TMSV) and barley stripe mosaic virus (BSMV), the core antigen of hepatitis B virus (HBV) and the nef gene product of human immunodeficiency virus-1 (HIV-1)—especially since nef has been shown to play an important role in the development of AIDS. (Kesstler, H. W. III, et al. *Cell* (1991) 65:651–662. Accordingly, inhibition of the prenylation of these target proteins or the post-prenylation reactions thereof is claimed to be inhibitory to the progress of these infections.

DISCLOSURE OF THE INVENTION

The invention provides methods to interfere with viral morphogenesis, production, release or uncoating both in vitro and in vivo. Agents which interfere with the prenylation of, or the post-prenylation reactions of, at least one viral protein are provided to infected cells to halt the viral infection. Such cells may be in culture or may be contained in an animal or plant subject.

Thus, in one aspect, the invention is directed to a method to inhibit viral morphogenesis, production, release or uncoating which method comprises effectively interfering with the prenylation of, or the post-prenylation reactions of, at least one viral protein. In another aspect, the invention is directed to an assay method for screening candidate drugs for their ability to inhibit prenylation. In a third aspect, the invention is directed to a method for treating viral infection by administering an agent effective to inhibit prenylation of, or the post-prenylation reactions of, a viral protein. In preferred embodiments, the viral protein is the large delta antigen of the hepatitis D virus, core antigen of HBV, or the nef protein of HIV.

BRIEF DESCRIPTION OF THE DRAWINGS

FIGS. 1A and 1B are photocopies of immunoblots of proteins obtained by lysis of viral-infected cells expressing viral proteins and treated with tritiated mevalonate.

FIGS. 2A and 2B are photocopies of immunoblots of proteins derived from lysates of cells containing wild type or mutant viral proteins and labeled with tritiated proline or mevalonate.

FIGS. 3A, 3B, 3C and 3D are photocopies of immunoblots of various cell supernatants containing viral proteins.

FIG. 4 is a diagrammatic representation of the progress of HDV morphogenesis.

MODES OF CARRYING OUT THE INVENTION

Hepatitis delta virus (HDV) infections cause both acute and chronic liver disease and can be fatal (1, 2). This RNA virus contains a 1.7 kb single-stranded circular genome and delta antigen, the only known HDV-encoded protein. These elements are encapsulated by a lipid envelope in which hepatitis B virus surface antigens are embedded (3), which explains why HDV infections occur only in the presence of an accompanying HBV infection (4, 5). Two isoforms of delta antigen exist in infected livers and serum (6, 7). This heterogeneity arises from a unidirectional mutation at a single nucleotide in the termination codon for delta antigen (codon 196: UAG→UGG), which occurs during replication (8). Thus, although small delta antigen is 195 amino acids long, large delta antigen is identical in sequence except that it contains an additional 19 amino acids at its COOH terminus. Although both forms of delta antigen contain the same RNA genome binding domain (9), they have dramatically different effects on genome replication. The small form is required for replication, whereas the large form is a potent trans-dominant inhibitor (10, 11).

The last four amino acids of large delta antigen are Cys-Arg-Pro-Gln-COOH (SEQ ID NO: 2). This COOH-terminal configuration, termed a CXXX (SEQ ID NO: 1) box (where C is cysteine and X is any amino acid), has been implicated as a substrate for prenyltransferases that add to the cysteine 15 (farnesyl) or 20 (geranylgeranyl) carbon moieties derived from mevalonic acid (12–14). The resulting hydrophobic modification may aid in membrane association of the derivatized protein, as suggested for p21 Ras (15, 16) and lamin B (12, 17). We have now demonstrated that large delta antigen is similarly modified.

Other virions also contain suitable target sequences for prenylation. These sequences are near the carboxy terminus of the viral protein targeted, and may be in the form of CXXX (SEQ ID NO: 1) boxes, but the cysteine may also be closer to the C-terminus, including a position as the C-terminal amino acid, as is the case of the core antigen of hepatitis B virus (HBV) and the nef gene product of HIV-1.

To determine whether large delta antigen is a a substrate for prenylation, we labeled three cell lines, SAG, LAG, and GP4F, with [$^3$H]mevalonic acid. GP4F cells are a derivative of NIH 3T3 cells (18). SAG (19) and LAG (20) cells are derivatives of GP4F cells that stably express the small and large delta antigens, respectively.

Labeled cell lysates were analyzed on immunoblots (FIG. 1A) to detect steady-state amounts of small and large delta antigen. The lysates were also subjected to immunoprecipitation with an antibody to the delta antigens (anti-delta), SDS polyacrylamide gel electrophoresis (SDS-PAGE), and fluorography (FIG. 1B).

In more detail, referring to FIG. 1, large delta antigen is shown to be prenylated in cultured cells. The cell lines SAG (19) (lane 1), LAG (20) (lane 2), and GP4F (18) (lane 3) were grown overnight in Lovastatin (25 $\mu$M) and (R,S)-[5-$^3$H]mevalonate (140 mM)) (30), and lysed in RIPA buffer [50 mM Tris (pH 7.5), 150 mM NaCl, 1% NP-40, 0.5% sodium deoxycholate, 0.1% SDS) (20). (A) Aliquots were subjected to immunoblot analysis (11). The blot was treated with serum from an HDV-infected patient that contained antibody to delta antigen ($\alpha$-$\delta$Ag) and horseradish peroxidase-conjugated rabbit antibody to human immunoglobulin G (IgG) (Promega), followed by chemiluminescence (Amersham) development. (B) Immunoprecipitates (with $\alpha$-$\delta$Ag) from cell extracts were subjected to SDS-PAGE and fluorography. As shown in FIG. 1, S, small delta antigen, L, large delta antigen. Molecular size markers are shown at the left (in kilodaltons).

Thus, the large, but not the small, antigen was labeled with [$^3$H]mevalonic acid, suggesting that large delta antigen undergoes prenylation in cultured cells.

We obtained similar results using in vitro translation reactions (13) performed in the presence of [$^3$H]proline or [$^3$H]mevalonate (FIG. 2). FIG. 2. also shows mutation of Cys$^{211}$ of large delta antigen to Ser and loss of prenylation. In vitro translation reactions were performed with rabbit reticulocyte lysates (Promega) in the presence of either (A) L-[2,3,4,5-$^3$H]proline (19 $\mu$M) (94 Ci/mmol, Amersham) or (B), [$^3$H]mevalonate (200 $\mu$M) (30). For (A) and (B), translation reactions contained small delta antigen mRNA (lane 1); large delta antigen mRNA (lane 2); water (lane 3); or large delta antigen (Cys$^{211}$→Ser) (20) mRNA (lane 4). A portion 20 $\mu$l) of each reaction was added to 1 ml of RIPA buffer, immunoprecipitated with $\alpha$-$\delta$Ag, and analyzed as described (FIG. 1).

Both the small and the large antigens were labeled with [$^3$H]proline (FIG. 2A), whereas only the large isoform was labeled with [$^3$H]mevalonate (FIG. 2B). To determine whether modification by [$^3$H]mevalonate was dependent on the presence of Cys$^{211}$ in the terminal CXXX (SEQ ID NO: 1) box, we constructed a mutant that contains a serine at this position (20). Cys$^{211}$ is the only cysteine in large delta antigen. Mutating Cys$^{211}$ to Ser did not interfere with the synthesis of large delta antigen (FIG. 2A) but abolished its modification by [$^3$H]mevalonate (FIG. 2B).

The specific type of mevalonate modification of large delta antigen appears to be geranylgeranyl rather than farnesyl (21). Although the first described CXXX (SEQ ID NO: 1) boxes contained aliphatic residues at the first and second positions after Cys, other types of amino acids can be found in prenylation sites (13, 14). It is not clear whether the COOH-terminal sequence Cys-Arg-Pro-Gln-COOH (SEQ ID NO: 2), which differs from that of previously described CXXX (SEQ ID NO: 1) boxes, implies the existence of a novel prenylation enzyme or whether it reflects a broader substrate specificity of known prenyltransferases.

For HDV particle formation, delta antigen and associated genomes are presumably targeted to cell membranes that contain HBV envelope proteins. We hypothesized that prenylation of large delta antigen could be involved in this process. We first examined whether large delta antigen was sufficient for HDV-like particle formation. HBV surface antigen (HBsAg) was expressed transiently in COS-7 cells together with small or large delta antigen. Virus-like particles consisting of delta antigen packaged into HBsAg-containing envelopes were analyzed by immunoprecipitation of clarified media supernatants with an antibody to HBsAg (anti-HBs).

FIG. 3 shows particle formation with large delta antigen and HBsAg parts. For panels (A) and (B), COS-7 cells were transiently transfected with the following plasmids: SV24H, which expresses HBV surface antigen (31), and SVLAg, which expresses small delta antigen (19) (lane 1); SV24H and SVL-large, which expresses large delta antigen (20) (lane 2); and calcium phosphate precipitate without DNA (lane 3). In (C) and (D), COS-7 cells were transfected with SV24H and SVL-large (lane 4); SV24H and SVL-large (Ser$^{211}$) (20) (lane 5); and calcium phosphate precipitate without DNA (lane 6). For (A) and (C), 48 hours after transfection, HBsAg-containing particles were immunoprecipitated from 2-ml aliquots of clarified media supernatants with anti-HBs (31) and subjected to immunoblot (with $\alpha$-$\delta$Ag) and chemiluminescence analyses as described (FIG. 1). For (B) and (D), the transfected cells were harvested in cell lysis buffer [50 mM Tris (pH 8.8), 2% SDS] with protease inhibitors (20), and aliquots subjected to protein immunoblot and chemiluminescence analyses. Molecular size markers are shown at the left (in kD).

The presence of delta antigen in the immunoprecipitates was assayed by immunoblot analysis (FIG. 3A). Although both small and large antigens were synthesized in the transfected cells (FIG. 3B), only the large isoform was incorporated into secreted HBsAg-containing particles (FIG. 3A). Similar selective packaging has been observed (22).

We then examined the function of mevalonate modification in this particle formation. One explanation for the preferred packaging of large delta antigen is that the small antigen lacks the CXXX (SEQ ID NO: 1) box and therefore cannot undergo modification. The Cys$^{211}$→Ser mutant of large delta antigen should behave like small delta antigen and not be packaged. This was indeed found to be the case. Whereas both wild-type and Ser$^{211}$ mutant large antigens were synthesized in transfected cells (FIG. 3D), only the wild-type form was packaged into particles (FIG. 3C). Thus, the mutated form of large delta antigen is not prenylated and cannot form particles with HBsAg.

Our results suggest that prenylation of large delta antigen is required for the formation and release of particles containing delta antigen and HBV surface antigens. The requirement of a prenylation site for productive viral infection is further suggested by other mutations of the CXXX (SEQ ID NO: 1) box (23) and by the conservation of $Cys^{211}$ and a CXXX (SEQ ID NO: 1) box motif among all sequenced HDV isolates (24).

The ability of large, but not small, delta antigen to be prenylated and packaged into virus particles further highlights the significance of the mutation-induced heterogeneity at the termination codon of the small delta antigen. During HDV replication, S genomes (encoding the small antigen) mutate to L genomes (encoding the large antigen). At least two effects attributable to this mutation can be distinguished (see FIG. 4). FIG. 4 shows the regulatory switch of S genomes to L genomes. During replication, S genomes encoding the small delta antigen mutate to L genomes, which encode the large delta antigen. This single base mutation has two effects on the COOH-terminus of delta antigen. The first is to change the nature of the COOH-terminal amino acid; Pro (P), which enhances genome replication (20), is replaced by Gln (Q), resulting in inhibition of genome replication. The second effect is the creation of a target prenylation site (CRPQ) (SEQ ID NO: 2), C, cysteine; R, arginine; P, proline; Q, glutamine.

Thus, the first effect is the conversion of an enhancer of genome replication (small delta antigen) into a potent trans-dominant inhibitor (large delta antigen) (10, 11). This dramatic difference in function appears to be determined solely by the nature of the COOH-terminal amino acid with proline being sufficient to confer enhancer activity (11, 25). The second effect is the addition of a CXXX (SEQ ID NO: 1) box to delta antigen, which allows the protein to be prenylated and presumably promotes its incorporation into HBsAg-containing particles. The combined effects of the switch from production of small to large delta antigen thus appear to have two roles: to suppress further genome replication and to promote the onset of packaging and virion morphogenesis.

Our results suggest prenylation as a new target for anti-HDV therapy and for antiviral therapy with respect to other viruses with prenylated proteins. Such therapy is directed at inhibiting virion morphogenesis, production, release and uncoating (functionally the reverse reaction of virion morphogenesis). In light of the increasingly apparent degeneracy of the four C-terminal amino acids required to function as a prenylation substrate, a cysteine located at any of these C-terminal positions is also considered to identify a potential target of antiprenylation therapy.

Several strategies designed to interfere with the prenylation stage of the HDV life cycle may be considered, including drugs that inhibit enzymes along the prenylation pathway, and CXXX (SEQ ID NO: 1) box analogs. Both therapies have been considered for the inhibition of ras-mediated oncogenic transformation (26). Tetrapeptides that correspond to the CXXX (SEQ ID NO: 1) box of p21 Ha-Ras inhibit prenylation of p21 Ha-Ras in vitro (27). Finally, the dual function of large delta antigen in the HDV life cycle suggests a further refinement of a proposed (11) defective interfering particle-(DIP) (28) like therapy aimed at cells infected with actively replicating S genomes. Because L genomes require a source of small delta antigen for replication (19, 29) but, once replicated, produce a potent trans-dominant inhibitor of further replication, a therapeutically administered L genome DIP could be specific for infected cells, as well as possess an inherent shut-off mechanism (11). If the L genome also contained the $Cys^{211}$ to Ser mutation, it could encode a delta antigen that not only inhibits replication but also affects packaging.

Accordingly, new approaches to antiviral therapy and inhibition of viral morphogenesis focus on inhibition of the prenylation of, or post-prenylation reactions of, at least one viral protein. This may be effected by contacting cells infected with the target virus with an effective amount of an agent which inhibits the prenylation of, or post-prenylation reactions of, at least one viral protein. Such agents include inhibitors of formation of the prenyl groups which are derivative of the mevalonate synthesis pathway. Other agents include decoys for the target sequence for prenylation, including small peptides, including tetrapeptides and other compounds which mimic the surroundings of the cysteine residue to be prenylated. For example, Reiss, Y., et al. *Cell* (1990) 62:81–88 report prenylation inhibition by C-A-A-X (SEQ ID NO: 3) tetrapeptides. As set forth above, the cysteine residue to be prenylated is generally found at the carboxy terminus of the target protein; although the most common target sequence involves a CXXX (SEQ ID NO: 1) box, cysteines positioned closer to the C-terminus may also be targeted; thus, the relevant peptides may include those of the form XCXX, XXCX, and XXXC (SEQ ID NO: 4, SEQ ID NO: 5 and SEQ ID NO: 6). Other agents include derivatives and mimics of prenyl groups themselves. Other suitable agents include inhibitors of the prenyltransferase enzymes and of enzymes that catalyze post-prenylation reactions.

Assay of Candidate Inhibitors

The present invention also provides a method to screen candidate drugs as prenylation inhibitors by taking advantage of the requirement for prenylation in order to effect secretion of certain prenylated proteins. For those proteins for which secretion requires prenylation, the assay can be conducted in a direct and simple manner. Cells that secrete, or that have been modified to secrete, a first protein whose secretion is dependent on prenylation are used as the experimental cells. A second protein which does not depend on prenylation for secretion is used as a control. This control protein may be secreted by the same or different host cells as the first protein. The candidate drug is applied to cells that secrete both proteins, or to matched sets of cells that secrete each. Secretion can readily be assessed by assaying the cell supernatants for the presence or absence of the first and second secreted proteins using, for example, routine ELISA assays. Successful candidate drugs will not inhibit the secretion of the control protein, but will inhibit the secretion of the protein in the test sample wherein prenylation is required for secretion.

The large delta antigen of HDV is a viral protein for which prenylation is a prerequisite for secretion. Thus, this protein forms, itself a key part of a useful test system for the assay. Cells that are modified to secrete a protein for which prenylation is not required can be used as controls. If large delta antigen is used as the test protein, it is advantageous to use HBsAg as the control protein in the same cell since HBsAg is also required for secretion of delta antigen.

The foregoing assay, of course, requires that the inhibitor interfere with the prenylation system for large delta antigen or for any other prenylation-controlled secreted protein used in the assay. A range of prenyl transferases and prenyl groups is known to apply to various proteins for which prenylation inhibitors are required or sought. Some of these proteins are not secreted, whether they are prenylated or not; one such example is the protein product of the ras oncogene.

Nevertheless, the assay system described can be employed to screen for inhibitors of prenylation in these nonsecreted proteins by providing the target "CXXX" (SEQ ID NO: 1) box characteristic of the nonsecreted protein in place of the corresponding "CXXX" (SEQ ID NO: 1) box of the secreted one. The resulting chimeric protein will exhibit the prenylation characteristics of the imported "CXXX" (SEQ ID NO: 1) box characteristic of the nonsecreted protein, but retain the ability of the host secreted protein to be passed to the supernatant for assay. Thus, the range of target proteins for which prenylation inhibitors are sought by use of the assay can be expanded to nonsecreted proteins.

The presence of a control system which provides secreted protein not dependent on prenylation is critical. The presence of this control allows candidate inhibitors which merely are toxic to the cells, or which inhibit secretion in general, to be discarded. Prenylation inhibitors identified by one of the variations of the above described assay are expected to find use not only in the inhibition of viruses, but also in other processes or disease states—including but not limited to cancer—in which a prenylated protein is found to be involved.

Evidently, prenylation of viral proteins is a prerequisite for additional post-prenylation reactions of the proteins such as proteolysis and carboxymethylation. The essential sequence of steps can be interfered with at the most convenient point for the viral protein in question.

Administration of the Inhibitors

Additional viral proteins subject to prenylation can be obtained by screening amino acid sequence data banks for viral proteins which contain a "CXXX" (SEQ ID NO: 1) box at the C-terminus. An illustrative list of such proteins includes, for example, specific proteins of HAV, HCV, HSV, CMV, VZV, influenza virus, plant viruses such as tobacco mosaic satellite virus and barley stripe mosaic virus, core antigen of hepatitis B virus and the nef gene product of HIV I, as set forth above. These candidates for suitable prenylation targets can be validated in a manner similar to that described above by providing labeled mevalonic acid to cells infected with or containing the appropriate viruses or viral gene products, and assessing the prenylation status of the viral proteins obtained using incorporation of label as the criterion. Furthermore, the role of prenylation in the morphogenesis of the respective virions, and its suitability as a target for anti-viral therapy, can also be validated in a manner similar to that described above.

If viral morphogenesis, production, release or uncoating are to be inhibited in culture, suitable host cells are used to culture the virus, and the agents used in inhibiting prenylation or post prenylation reactions added to the medium. If the infected cells are contained in an animal subject, such as a mammalian subject or in particular a human or other primate subject, the agent used for the prenylation inhibition is generally introduced as a pharmaceutical formulation. Suitable formulations depending on the nature of the agent chosen may be found in *Remington's Pharmaceutical Sciences*, latest edition, Mack Publishing Co., Easton, Pa. The routes of administration include standard such routes, including administration by injection, oral administration, and transmucosal and transdermal administration. The choice of formulation will depend on the route of administration as well as the agent chosen. Suitable mixtures of agents can also be used as active ingredients. For administration to plants, formulations which are capable of conducting the active ingredients into plant cells are used as carriers.

The following references are listed according to the number which refers to them in the body of the specification:

REFERENCES AND NOTES

1. Rizzetto, M., *Hepatology* (1983) 3:729.
2. Hoffnagle, J. H., *J. Am. Med. Assoc.* (1989) 261:1321.
3. Bonino, F., et al., *Infect. Immun.* (1984) 43:1000.
4. Rizzetto, M., et al., *J. Infect. Dis.* (1980) 141:590.
5. Rizzetto, M., et al., *Proc. Natl. Acad. Sci. U.S.A.* (1980) 77:6124.
6. Bergmann, K. F., et al., *J. Infect. Dis.* (1986) 154:702.
7. Bonino, F., et al., *J. Virol* (1986) 58:945.
8. Luo, G., et al., ibid. (1990) 64:1021.
9. Lin, J.-H., et al., ibid., p. 4051.
10. Chao, M., et al., ibid., p. 5066.
11. Glenn, J. S., et al., ibid. (1991) 65:2357.
12. Glomset, J. A., et al., *Trends Biochem. Sci.* (1990) 15:139.
13. Maltese, W. A., *FASEB J.* (1990) 4:3319.
14. Moores, S. L., et al., *J. Biol. Chem.* (1991) 266:14603.
15. Hancock, J. F., et al., *Cell* (1989) 57:1167.
16. Schafer, W. R., et al., *Science* (1989) 245:379.
17. Beck, L. A., et al., *J. Cell Biol.* (1988) 107:1307.
18. Ellens, H., et al., *Methods Cell Biol.* (1989) 31:155.
19. Glenn, J. S., et al., *J. Virol.* (1990) 64:3104. SAG cells are identical to GAG cells.
20. Glenn, J. S., thesis, University of California, San Francisco (1992).
21. Glenn, J. S., et al., unpublished data.
22. Wang, C. J., et al., *J. Virol.* (1991) 65:6630; Ryu, W.-S., et al., ibid. in press; Sureau, C., personal communication.
23. Ryu, W.-S., et al., in preparation.
24. Of 14 independent viral isolates sequenced, 13 code for Cys-Arg-Pro-Gln-COOH and 1 codes for Cys-Thr-Pro-Gln-COOH as the four terminal amino acids of large delta antigen [Wang, K.-S., et al., *Nature* (1986) 323:508; Makino, S., et al., ibid. (1987) 329:343; Kuo, M. Y. P., et al., *J. Virol.* (1988) 62:1855; Saldanha, J. A. et al., *J. Gen. Virol.* (1990) 71:1603; Xia, Y.-P., et al., (1990) 178:331; Imazeki, F. et al., *J. Virol.* (1990) 64:5594; Chao, Y.-C., et al., *Hepatology* (1991) 13:345; Deny, P. et al., *J. Gen. Virol.* (1991) 72:735].
25. We have recently found that specific mutation of the COOH-terminal Gln of large delta antigen to Pro converted the protein from an inhibitor to an enhancer of genome replication (20).
26. Gibbs, J. B., *Cell* (1991) 65:1.
27. Reiss, Y., et al., ibid. (1990) 62:81.
28. Ramig, R. F., in *Virology*, Fields, B. N., et al., Eds. (Raven, N.Y., 1990), pp. 112–122.
29. Kuo, M. Y.-P., et al., *J. Virol.* (1989) 63:1945.
30. (R,S)-[5-$^3$H]mevalonate (4 to 18.8 Ci/mmol) was synthesized according to the method of R. K. Keller, *J. Biol. Chem.* (1986) 261:12053.
31. Bruce, V. et al., *J. Virol.* (1991) 65:3813.
32. We thank J.-J. Gonvers for providing human anti-delta antigen serum, A. Alberts for providing Lovastatin, and J. M. bishop, H. Bourne, and D. Ganem for helpful discussions and critical reading of the manuscript. J. M. W. is a recipient of an NIH grant and J. S. G. was supported by the Medical Scientist Training Program.

I claim:

1. A method to treat a viral infection in a subject via inhibiting the prenylation of a protein contained in the virus infecting said subject, which method comprises administering to said subject an agent selected from the group consisting of an agent that mimics the amino acid sequence of a "CXXX" (SEQ ID NO:1), "XCXX" (SEQ ID NO:4), "XXCX" (SEQ ID NO:5), or "XXXC" (SEQ ID NO: 6) box as it occurs in said viral protein, and an inhibitor of a prenyl transferase.

2. The method of claim 1, wherein said agent mimics the amino acid sequence of the "CXXX" (SEQ ID NO:1), "XCXX" (SEQ ID NO:4), "XXCX" (SEQ ID NO:5), or "XXXC" (SEQ ID NO: 6) box as it occurs in said protein.

3. The method of claim 1, wherein said agent is an inhibitor of a prenyltransferase.

4. The method of claim 1, wherein said subject is an animal or a plant.

5. The method of claim 4, wherein said animal is a mammal.

6. The method of claim 5, wherein said mammal is a human.

7. The method of claim 5, wherein said mammal is a non-human primate.

8. The method of claim 1, wherein the prenyl transferase is a farnesyltransferase.

9. The method of claim 1, wherein the prenyl transferase is a geranylgeranyltransferase.

* * * * *

UNITED STATES PATENT AND TRADEMARK OFFICE
CERTIFICATE OF CORRECTION

PATENT NO.    : 6,627,610 B1
DATED         : September 30, 2003
INVENTOR(S)   : Jeffrey Glenn It is certified that error appears in the above-identified patent and that said Letters Patent is hereby corrected as shown below:

Column 12,
Line 37, please replace claims 8 and 9 as follows:

-- 8.   The method of claim 1, wherein said agent is an inhibitor of a farnesyltransferase.

9.   The method of claim 1, wherein said agent is an inhibitor of a geranylgeranyltransferase.--

Line 42, add the following claims 1-42:

--10.   The method of claim 1, wherein said agent mimics the amino acid sequence of the "CXXX" (SEQ ID NO:1) box as it occurs in said protein.

11.   The method of claim 1, wherein said agent mimics the amino acid sequence of the "XCXX" (SEQ ID NO:4) box as it occurs in said protein.

12.   The method of claim 1, wherein said agent mimics the amino acid sequence of the "XXCX" (SEQ ID NO:5) box as it occurs in said protein.

13.   The method of claim 1, wherein said agent mimics the amino acid sequence of the "XXXC" (SEQ ID NO: 6) box as it occurs in said protein.

14.   The method of claim 3, wherein said subject is an animal or a plant.

15.   The method of claim 14, wherein said animal is a mammal.

16.   The method of claim 15, wherein said mammal is a human.

17.   The method of claim 15, wherein said mammal is a non-human primate.

18.   The method of claim 8, wherein said subject is an animal or a plant.

UNITED STATES PATENT AND TRADEMARK OFFICE
CERTIFICATE OF CORRECTION

PATENT NO. : 6,627,610 B1
DATED : September 30, 2003
INVENTOR(S) : Jeffrey Glenn It is certified that error appears in the above-identified patent and that said Letters Patent is hereby corrected as shown below:

Column 12 (cont'd),

19. The method of claim 18, wherein said animal is a mammal.

20. The method of claim 19, wherein said mammal is a human.

21. The method of claim 19, wherein said mammal is a non-human primate.

22. The method of claim 9, wherein said subject is an animal or a plant.

23. The method of claim 22, wherein said animal is a mammal.

24. The method of claim 23, wherein said mammal is a human.

25. The method of claim 23, wherein said mammal is a non-human primate.

26. The method of claim 10, wherein said subject is an animal or a plant.

27. The method of claim 26, wherein said animal is a mammal.

28. The method of claim 27, wherein said mammal is a human.

29. The method of claim 27, wherein said mammal is a non-human primate.

30. The method of claim 11, wherein said subject is an animal or a plant.

31. The method of claim 30, wherein said animal is a mammal.

32. The method of claim 31, wherein said mammal is a human.

UNITED STATES PATENT AND TRADEMARK OFFICE
CERTIFICATE OF CORRECTION

PATENT NO. : 6,627,610 B1
DATED : September 30, 2003
INVENTOR(S) : Jeffrey Glenn It is certified that error appears in the above-identified patent and that said Letters Patent is hereby corrected as shown below:

Column 12 (cont'd),

33. The method of claim 31, wherein said mammal is a non-human primate.

34. The method of claim 12, wherein said subject is an animal or a plant.

35. The method of claim 34, wherein said animal is a mammal.

36. The method of claim 35, wherein said mammal is a human.

37. The method of claim 35, wherein said mammal is a non-human primate.

38. The method of claim 24, wherein said subject is an animal or a plant.

39. The method of claim 38, wherein said animal is a mammal.

40. The method of claim 39, wherein said mammal is a human.

42. The method of claim 39, wherein said mammal is a non-human primate.--

Signed and Sealed this

Fourteenth Day of September, 2004

JON W. DUDAS
*Director of the United States Patent and Trademark Office*

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<221> NAME/KEY: VARIANT
<222> LOCATION: 2,3,4
<223> OTHER INFORMATION: Xaa = Any amino acid
<223> OTHER INFORMATION: consensus sequence for directing protein
      prenylation

<400> SEQUENCE: 1

Cys Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: consensus sequence for directing protein
      prenylation

<400> SEQUENCE: 2

Cys Arg Pro Gln
1

<210> SEQ ID NO 3
<211> LENGTH: 4
<212> TYPE: PRT
<213> ORGANISM: Artificial Sequence
<220> FEATURE:
<221> NAME/KEY: VARIANT
<222> LOCATION: 4
<223> OTHER INFORMATION: Xaa = Any amino acid
<223> OTHER INFORMATION: consensus sequence for directing protein
      prenylation

<400> SEQUENCE: 3

Cys Ala Ala Xaa
1

<210> SEQ ID NO 4
<211> LENGTH: 4
<212> TYPE: PRT
<213> ORGANISM: Artificial Sequence
<220> FEATURE:
<221> NAME/KEY: VARIANT
<222> LOCATION: 1,3,4
<223> OTHER INFORMATION: Xaa = Any amino acid
<223> OTHER INFORMATION: consensus sequence for directing protein
      prenylation

<400> SEQUENCE: 4

Xaa Cys Xaa Xaa
1

<210> SEQ ID NO 5
<211> LENGTH: 4
<212> TYPE: PRT
<213> ORGANISM: Artificial Sequence
<220> FEATURE:
<221> NAME/KEY: VARIANT
<222> LOCATION: 1,2,4
<223> OTHER INFORMATION: Xaa = Any amino acid
<223> OTHER INFORMATION: consensus sequence for directing protein -continued

```
      prenylation

<400> SEQUENCE: 5

Xaa Xaa Cys Xaa
 1

<210> SEQ ID NO 6
<211> LENGTH: 4
<212> TYPE: PRT
<213> ORGANISM: Artificial Sequence
<220> FEATURE:
<221> NAME/KEY: VARIANT
<222> LOCATION: 1,2,3
<223> OTHER INFORMATION: Xaa = Any amino acid
<223> OTHER INFORMATION: consensus sequence for directing protein
      prenylation

<400> SEQUENCE: 6

Xaa Xaa Xaa Cys
 1
```